United States Patent
Xiao et al.

(10) Patent No.: US 7,576,249 B2
(45) Date of Patent: *Aug. 18, 2009

(54) TOLUENE DISPROPORTIONATION PROCESS UTILIZING MILD SULFIDING DURING STARTUP

(75) Inventors: Xin Xiao, Houston, TX (US); Becky Fussell, Pasadena, TX (US); James Butler, League City, TX (US); Brandi Gomez, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 559 days.

This patent is subject to a terminal disclaimer.

(21) Appl. No.: 11/030,707

(22) Filed: Jan. 6, 2005

(65) Prior Publication Data

US 2006/0149106 A1 Jul. 6, 2006

(51) Int. Cl.
*C07C 6/12* (2006.01)
(52) U.S. Cl. ..................................... 585/475
(58) Field of Classification Search .................. 585/475
See application file for complete search history.

(56) References Cited

U.S. PATENT DOCUMENTS

| | | | |
|---|---|---|---|
| 3,239,450 A | 3/1966 | Linquist et al. | |
| 3,436,174 A | 4/1969 | Sand | |
| 3,476,821 A | 11/1969 | Brandenburg et al. | |
| 3,480,539 A | 11/1969 | Voorhles et al. | |
| 3,780,122 A | 12/1973 | Pollitzer | |
| 3,912,659 A * | 10/1975 | Brandenburg et al. | 502/66 |
| 4,956,511 A | 9/1990 | Butler et al. | |
| 5,387,732 A | 2/1995 | Shamshoum et al. | |
| 5,475,180 A | 12/1995 | Shamshoum et al. | |
| 5,865,986 A | 2/1999 | Buchanan et al. | |
| 6,504,076 B1 | 1/2003 | Xiao et al. | |
| 6,706,937 B2 | 3/2004 | Xiao et al. | |
| 2003/0092950 A1 | 5/2003 | Xiao et al. | |

\* cited by examiner

*Primary Examiner*—Thuan Dinh Dang
(74) *Attorney, Agent, or Firm*—Tenley R. Krueger

(57) ABSTRACT

A process for the disproportionation of toluene over a nickel-modified mordenite catalyst which has been pretreated with mild sulfiding procedure. The sulfur dose is employed in a minor amount relative to the nickel content of the catalyst. The modified mordenite catalyst is contacted with a sulfur-containing compound such as hydrogen sulfide or dimethyldisulfide (DMDS) under pretreatment conditions involving a temperature of at least 100° C. The sulfur-containing compound is employed in a relatively small amount to passivate only a minor portion of the active nickel sites. A toluene-containing feedstock is brought into contact with the pretreated catalyst under conditions effective for the disproportionation of toluene and a disproportionation product is removed from contact with the catalyst. The mordenite catalyst contains nickel in an amount within the range of 0.1-2 wt. %. The catalyst may contain another metal such as palladium or platinum, or a lanthanide series metal such as lanthanum or cerium. Pretreatment of the catalyst may be carried out by flowing a fluid pretreatment stream having a sulfur component into contact with the catalyst. The pretreatment stream comprises hydrogen sulfide or a thio compound which is converted to hydrogen sulfide under the pretreatment conditions.

9 Claims, 2 Drawing Sheets

TOLUENE DISPROPORTIONATION PROCESS UTILIZING MILD SULFIDING DURING STARTUP

FIELD OF THE INVENTION

This invention relates to the disproportionation of alkylaromatic feedstreams and more particularly to the disproportionation of toluene-containing feedstocks employing pretreated nickel-modified mordenite catalysts.

BACKGROUND OF THE INVENTION

It is often desirable to convert alkyl aromatic compounds through disproportionation reactions to produce disproportionation products which can include unsubstituted aromatic compounds as well as alkyl aromatic compounds, including monoalkyl aromatics and polyalkyl aromatics, and mixtures thereof. Such disproportionation reactions may be employed to produce disproportionation products comprising benzene and mixtures of alkyl and polyalkyl benzenes. While such disproportionation reactions may be employed to convert relatively high molecular weight alkyl aromatics, one important disproportionation reaction involves the disproportionation of toluene to benzene and xylene. The disproportionation of toluene involves a well known transalkylation reaction in which toluene is converted to benzene and xylene in accordance with the following reaction, which is mildly exothermic:

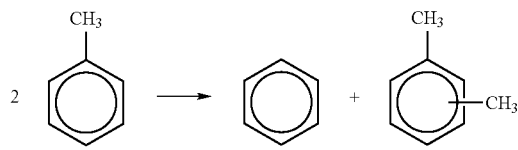

Mordenite is one of a number of catalysts which can be employed in the transalkylation of alkylaromatic compounds. Mordenite is a crystalline aluminosilicate zeolite having a network of silicon and aluminum atoms interlinked in its crystalline structure through oxygen atoms. For a general description of mordenite catalysts, reference is made to Kirk-Othmer Encyclopedia of Chemical Technology, $3^{rd}$ Edition, 1981, under the heading "Molecular Sieves," vol. 15, pages 638-643. Mordenite, as found in nature or as synthesized, typically has a relatively low silica to alumina mole ratio of about 10 or less. Such conventionally structured mordenite catalysts can be employed in the disproportionation of toluene. However, aluminum deficient mordenite catalysts having substantially lower alumina contents can also be employed in the disproportionation of toluene.

Aluminum deficient mordenite catalysts have a silica/alumina ratio greater than 10 and may sometimes range up to about 100. Such low alumina mordenites may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al. U.S. Pat. No. 3,780,122 to Pollitzer discloses the transalkylation of toluene using a mordenite zeolite having a silica/alumina ratio greater than 10 which is obtained by acid extraction of a mordenite zeolite having a silica/alumina ratio of less than 10.

The disproportionation of toluene feedstocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art indicates that while relatively high temperatures can be employed for the high aluminum mordenites (low silica to alumina ratios), somewhat lower temperatures should be employed for the low alumina mordenites. Thus, where mordenite catalysts having high silica/alumina ratios have been employed in the transalkylation of alkylaromatics, it has been the practice to operate toward the lower end of the temperature range. It is also a common practice in this case to promote the catalyst with a catalytically active metallic content, as disclosed, for example, in U.S. Pat. No. 3,476,821 to Brandenburg. Metal promoters are said to substantially increase activity and catalyst life and may be incorporated by treatment of the mordenite with metal sulfides such as nickel sulfide.

Hydrogen may be supplied along with the toluene to the reaction zone. While the disproportionation reaction (1) is net of hydrogen, the use of a hydrogen co-feed is generally considered to prolong the useful life of the catalyst, as disclosed, for example, in the above-identified patent to Brandenburg. The amount of hydrogen supplied, which can be measured in terms of the hydrogen/toluene mole ratio or in terms of a standard liter of hydrogen per liter of feedstock, is generally shown in the prior art to increase as temperature increases. Normally, the hydrocarbon feedstock supplied to the toluene disproportionation reaction zone is of extremely high purity. Typically, feedstocks having a toluene content of 90-100 wt. % are supplied to the reaction zone. Usually, it is considered desirable to maintain the toluene content in excess of 99 wt. % (less than 1% impurities) for toluene disproportionation processes.

SUMMARY OF THE INVENTION

In accordance with the present invention, there is provided a novel process for the disproportionation of a feedstock containing at least one alkyl aromatic compound over a nickel-modified mordenite catalyst which has been pretreated with mild sulfiding procedure. A preferred application of the present invention involves the disproportionation of toluene to produce a transalkylated product containing benzene and xylene. The feedstock may take the form of a relatively pure toluene stream or the feedstock may contain higher molecular weight alkyl aromatic components. The sulfur dose is employed in a minor amount relative to the nickel content of the nickel-modified mordenite catalyst. In carrying out the invention, a nickel-modified mordenite catalyst is contacted with a sulfur-containing compound such as hydrogen sulfide or dimethyldisulfide (DMDS) under pretreatment conditions involving a temperature of at least 100° C. The sulfur-containing compound is employed in a relatively small amount so that only a minor portion of the active nickel sites are passivated. Subsequent to pretreatment of the catalyst, a toluene-containing feedstock is brought into contact with the pretreated catalyst under conditions effective for the disproportionation of toluene and a transalkylation product containing benzene and xylene is removed from contact with the nickel-modified mordenite disproportionation catalyst.

In a preferred embodiment of the invention, the mordenite catalyst contains nickel in an amount within the range of 0.1-2 wt. %. The modified catalyst may contain another metal in addition to the nickel. The additional metal may be another Group 10 metal other than nickel, that is, palladium or platinum, or may be a lanthanide series metal such as lanthanum or cerium.

Pretreatment of the nickel-modified mordenite catalyst may be carried out by flowing a fluid pretreatment stream having a sulfur component into contact with the catalyst. The pretreatment stream comprises hydrogen sulfide or a thio compound which is converted to hydrogen sulfide under the pretreatment conditions. The sulfur component preferably is used in an amount to provide a sulfur content relative to the nickel content of the catalyst of at least 3 mole %, or stated in terms of mole ratios, a sulfur to nickel mole ratio of at least 1:30. Higher amounts of sulfur may be employed with further beneficial results occurring as the total sulfur content reaches about 10 mole % of the nickel in the catalyst. Even greater amounts of sulfur may be employed, although usually with no further beneficial results, in amounts providing a sulfur dose of 100 mole % of the nickel or above. In terms of the sulfur to nickel mole ratio achieved during the pretreating procedure, the total sulfur to nickel mole ratio thus will be within the range of about 1:30 to 1:1 and preferably within the range of 1:30 to 1:10. Normally, only a very small amount of the sulfur-containing component is employed in the pretreatment stream. Preferably, the pretreatment stream has a sulfur content providing an equivalent hydrogen sulfide concentration within the range of 0.01-20 vol. %. Preferably, the pretreatment stream comprises hydrogen, having a hydrogen sulfide content of at least 100 ppm or a thio compound providing an equivalent hydrogen sulfide content of at least 100 ppm. Suitable pretreatment streams comprise hydrogen containing a sulfur compound selected from the group consisting of hydrogen sulfide, carbon disulfide, dimethylsulfide, dimethyldisulfide and mixtures thereof in relatively minor amounts as indicated above.

In a preferred embodiment of the invention, there is provided a catalytic reaction zone containing at least one catalyst bed comprising a nickel-modified mordenite disproportionation catalyst. A first temperature within the reaction zone falling within the range of 100-350° C. is established and the nickel-modified catalyst in the catalyst bed is reacted with hydrogen sulfide to passivate active metal sites in the catalyst. A toluene-containing feedstock is supplied to the reaction zone and into contact with the catalyst bed. The temperature of the catalyst bed within the reaction zone is then increased to a higher temperature, within the range of 300-450° C. so that the temperature and pressure conditions are effective to carry out the disproportionation of the toluene in the presence of the nickel-modified disproportionation catalyst. The disproportionation production containing benzene and xylene is recovered from the reaction zone. The passivation of the minor amount of nickel sites by the hydrogen sulfide treatment provides for a disproportionation product having a nonaromatic content relative to the reaction effluent, which is less than 1.0 wt. %. In addition, the toluene disproportionation reaction in the reaction zone is characterized by an exotherm of relatively low intensity moving through the catalyst bed. Specifically, the exotherm moving through the catalyst bed is less than one-half of the corresponding exotherm produced by a corresponding toluene disproportionation reaction in the presence of a nickel-modified mordenite catalyst which has not been pretreated by contact with hydrogen sulfide. Preferably, the exotherm is no more than one-fifth of the corresponding exotherm produced by toluene disproportionation in the presence of the identical nickel-modified mordenite catalyst that has not been pretreated by contact with hydrogen sulfide.

DETAILED DESCRIPTION OF THE INVENTION

Figure 1:
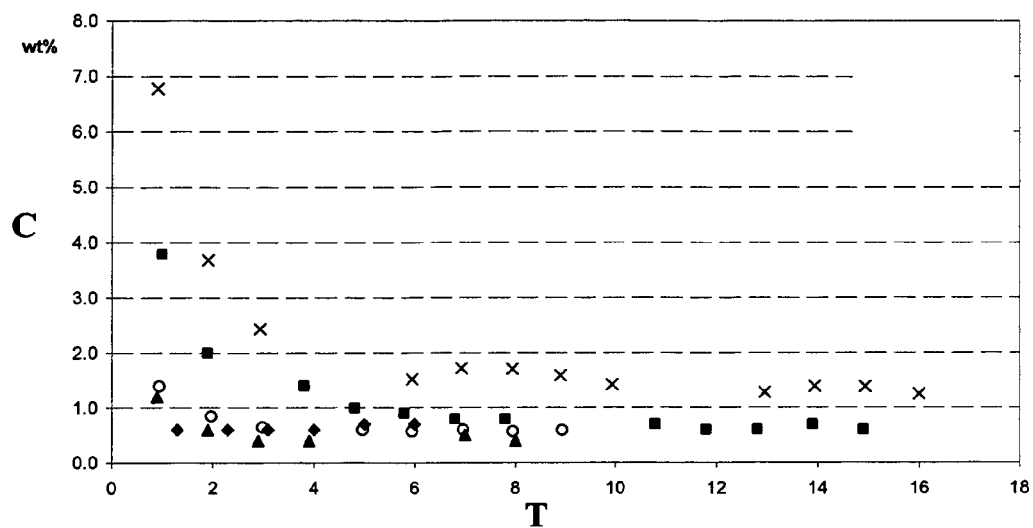
FIG. 1 is a graphical presentation showing the nonaromatics content of the product of the toluene disproportionation procedure at various levels of the amounts sulfur is employed in a sulfur pre-treatment procedure.

The present invention involves a process for the disproportionation of an alkyl benzene or mixtures of alkyl benzenes to produce benzene and polyalkyl benzene. While the invention may be employed in the disproportionation of relatively heavy aromatics, that is $C_{8+}$ aromatics and particularly $C_8$-$C_{12}$ alkyl aromatics, the present invention is particularly suitable in the disproportionation of toluene, which may be carried out alone or in conjunction with the disproportionation of heavier alkyl aromatics. For example, a mixture of trimethylbenzene and toluene may be subject to transalkylation to produce xylene. Alternatively, the conversion of such heavier aromatics can be carried out not only in conjunction with the disproportionation of toluene, but also employing feedstreams in which no toluene is present. By way of example, ethylbenzene can be subjected to a disproportion reaction to produce benzene and diethylbenzene. For a general description of disproportionation reactions to which the present invention may be applied, reference is made to U.S. Pat. No. 6,504,076 to Xiao et al., the entire disclosure of which is incorporated by reference. As noted previously, a preferred application is in the disproportionation of toluene with or without the presence of higher alkyl aromatics and the invention will be described in detail with reference to toluene disproportionation.

A specific application of the present invention provides a process that can be employed to disproportionate toluene to produce benzene and xylene, while reducing the magnitude of the exotherm which moves through the catalyst bed and enhancing the toluene disproportionation reaction while minimizing the production of non-aromatic byproducts. The toluene disproportionation catalyst employed in the present invention is a nickel-modified mordenite, such as disclosed in U.S. Pat. No. 6,706,937, the entire disclosure of which is incorporated herein by reference. The nickel mordenite catalyst typically has a nickel content within the range of 0.1-2 wt. % and may also include metals such as other Group 10 metals, such as palladium and platinum and also lanthanide series metals, specifically lanthanum and cerium. Thus, the nickel-modified mordenite catalyst may contain, in addition to the nickel, a second metal selected from a group consisting of a Group 10 metal other than nickel and at least one lanthanide series metal. Suitable disproportionation procedures and mordenite catalysts which can be employed in the present invention are also disclosed in U.S. Pat. Nos. 4,956,511, 5,387,732 and 5,475,180, the entire disclosures of which are incorporated herein by reference.

The mordenite catalyst employed in the present invention may be natural mordenites of relatively low silica/alumina ratios of about 10 or less. Such catalysts are disclosed in the aforementioned Kirk-Othmer Encyclopedia of Chemical Technology, $3^{rd}$ Edition, 1991, vol. 15, pp. 638-643, the entire disclosure of which is incorporated herein by reference. Alternatively, alumina-deficient mordenite catalysts typically having a silica/alumina mole ratio within the range of about 15-200 can be used in carrying out the present invention.

A suitable nickel-modified mordenite catalyst which can be employed in the present invention comprises a catalyst in the form of extruded prills, which comprise about 70-80% of the zeolite mordenite and about 20-30% of a binder, normally in the form of alumina, which is composited with the zeolitic mordenite. In manufacturing such catalysts, the mordenite and binder are composited together and then extruded and dried, followed by calcination to further dry out the mordenite. The catalyst is then impregnated with nickel by any suitable technique such as disclosed in the aforementioned U.S. Pat. No. 4,956,511 to Butler et al.

While applicants' invention is not to be limited by theory, it is believed that the result of the nickel treatment is that a large amount, perhaps 95-97% of the nickel, is impregnated into the mordenite itself with the remainder, about 3-5% of the nickel, incorporated with the alumina binder or catalyst outside surface. It is believed that the small amount of nickel on the binder is the primary source of undesirable byproducts in the toluene disproportionation reaction and that the sulfur treatment employed in the present invention functions to primarily passivate the nickel on the binder with an attendant decrease in the reaction exotherm and the hydrogenated byproducts.

In order to passivate only a small fraction of the nickel incorporated into the mordenite catalyst, it is desirable to employ hydrogen sulfide, or a hydrogen sulfide-producing reactant, in a relatively small amount. Hydrogen sulfide can be applied directly to the disproportionation reactor containing the nickel-modified mordenite. In this case, it will normally be desired to incorporate a relatively small amount of hydrogen sulfide in gaseous hydrogen supplied in a start-up procedure for the disproportionation reaction. Thus, a hydrogen stream containing about 0.01-20 vol. % hydrogen sulfide may be employed. The pretreatment procedure is conducted at an elevated temperature, typically within the range of 100-450° C. Rather than injecting hydrogen sulfide directly, a hydrogen stream containing a relative amount of a thio compound such as mercaptans and the like which convert to hydrogen sulfide under the conditions involved in pretreatment of the catalyst bed can be employed. Thus, thio compounds such as dimethylsulfide, dimethyldisulfide and carbon disulfide may be incorporated into the initially injected hydrogen stream during the start-up procedure. Mixtures of mercaptans may also be employed. In addition rather than employing a hydrogen pretreatment to incorporate the hydrogen sulfide into contact with the nickel-modified mordenite, thio compounds may be incorporated into an initial toluene stream supplied to the reactor at a temperature that is less than or equal to the temperature at which the toluene disproportionation reaction is carried out. By way of example, an initial toluene feed at a temperature of about 150-350° C. may be modified by the inclusion of a mercaptan such as dimethyldisulfide in a concentration of about 850 ppm. This enables the desired passivication of the desired nickel sites to be accomplished before the toluene disproportionation temperature is reached in order to minimize the production of undesirable byproducts such as hydrogenated aromatic compounds. Regardless of whether the hydrogen sulfide is introduced directly or indirectly through the use of a thio compound as described above, it will be preferred to provide an overall quantitative amount of sulfur to provide a sulfur/nickel mole ratio of at least 1:30, preferably within the range of 1:30 to 1:2, and more preferably within the range of 1:10 to 1:2. This sulfur/nickel mole ratio may range up to 1:1. Higher quantities of sulfur may be used but usually with no further benefit.

When a thio compound such as dimethylsulfide or dimethyldisulfide is employed as a source of hydrogen sulfide, the equivalent hydrogen sulfide concentration of the thio compound can be determined from the stoichiometry of the reaction by which the sulfur compound converts to hydrogen sulfide in the hydrogen environment. For example, carbon disulfide, dimethylsulfide and dimethyldisulfide react in the presence of hydrogen to produce hydrogen sulfide in accordance with the following relationships:

$$CS_2 + 4H_2 \rightarrow 2H_2S + CH_4 \tag{2}$$

$$(CH_3)_2S + 2H_2 \rightarrow H_2S + 2CH_4 \tag{3}$$

$$(CH_3)_2S_2 + 3H_2 \rightarrow 2H_2S + 2CH_4 \tag{4}$$

The amount of the sulfur compound to be employed can be calculated in accordance with the appropriate reaction, assuming the reaction is driven to 100% completion. For example, as indicated by reaction (2) above, one mole of carbon disulfide reacts with four moles of hydrogen to produce two moles of hydrogen sulfide. Thus, the equivalent amount of carbon disulfide to hydrogen sulfide is one-half of the actual hydrogen sulfide concentration. The amounts of other compounds to be employed also can be determined in accordance with this method of calculation. For example, reaction 3 for dimethylsulfide and reaction 4 for dimethyldisulfide indicate equal molar or one-half of the actual hydrogen sulfide concentration respectively.

The toluene disproportionation reaction may be carried out under conditions to provide toluene conversion within the range of about 40-55% as disclosed in the aforementioned U.S. Pat. No. 6,706,937. Conversion can be at the rate of about 46-47% when employing a nickel-modified mordenite catalyst having a nickel content of about 1 wt. %. In general, the process parameters disclosed the aforementioned U.S. Pat. No. 6,706,937 can be employed in the present invention with the important proviso that hydrogen sulfide, or a hydrogen sulfide equivalent of a thio compound, is employed in relatively small concentrations and total amounts as described herein in order to achieve a relatively low exotherm and low byproducts content.

Using as a standard a nickel-modified mordenite catalyst containing 1% nickel in a toluene disproportionation reaction zone operating at a temperature of about 360° C. and 40 atmospheres of pressure, an exotherm can be expected to be developed providing an incremental increase of 20-150° C. In normal commercial operations, an exotherm of this magnitude requires the injection of additional toluene as a quench fluid in order to cool off the catalyst bed and prevent the reaction from running away. By employing hydrogen sulfide or hydrogen sulfide equivalent such as dimethyldisulfide (DMDS), the exotherm developed in the catalyst bed will be less than one-half the standard exotherm (without the $H_2S$ pretreatment). Preferably, the exotherm can be minimized to a level where it is no more than one-fifth of the corresponding exotherm produced by the toluene disproportionation reaction when carried out over the corresponding nickel mordenite catalyst which has not been pretreated by hydrogen sulfide. This is achieved by minimize the ring hydrogenation reactions that lead to the formation of heat and nonaromatics. By employing the mentioned mild sulfiding, the nonaromatics byproduct will be less than one-half the standard nonaromatics (without the mild sulfiding).

In experimental work respecting the present invention, toluene disproportionation runs were carried out employing two nickel mordenite catalysts which were pre-sulfided with hydrogen sulfide or DMDS. Varying amounts of the sulfiding agents were used to provide sulfur to nickel mole ratios varying from 3% to 100%. The results were measured in terms of the nonaromatics content of the product of the toluene disproportionation procedure and the average catalysts bed temperature over the time of run. The catalysts employed in this experimental work are identified as Catalyst A and Catalyst B. Catalysts A and B are both nickel modified mordenites made out of different commercial batches. Both Catalyst A and B have a nickel content of 1.0 wt. % and a silica/alumina mole ratio of 20.

In a first set of experiments, Catalyst A was used without pre-sulfiding and with pre-sulfiding at 250° C. and 600 psig with a hydrogen flow rate of 2000 gas hourly space velocity (GHSV) in different doses of hydrogen sulfide or DMDS to provide a total sulfur treatment of the nickel ranging from 3-100 mole % of the nickel. The experimental results are shown in FIG. 1 in which the nonaromatics content of the liquid product in wt. % is plotted on the ordinate verses the time on stream T in days on the abscissa. In FIG. 1, the results obtained with the catalyst without pre-sulfiding (no sulfur) are indicated by data points ■. The data points for mole % sulfur relative to nickel employing hydrogen sulfide are indicated by x and the corresponding data points for 10% mole % total sulfur provided by DMDS are indicated by ○. The corresponding data points for 25 mole % of sulfur provided by hydrogen sulfide and 100 mole % of sulfur provided by hydrogen sulfide are indicated by ▲ and a ♦ respectively. As can be seen by the experimental work reported in FIG. 1, sulfur doses ranging from 10 to 100 mole % (corresponding to a sulfur to nickel mole ratio of 1:10 to 1:1) produced about the same relatively low nonaromatics content during start-up whereas the catalyst without sulfiding and the catalyst sulfided with 3 mole % sulfur resulting from hydrogen sulfide treatment showed substantially higher nonaromatic liquid content.

Figure 2:
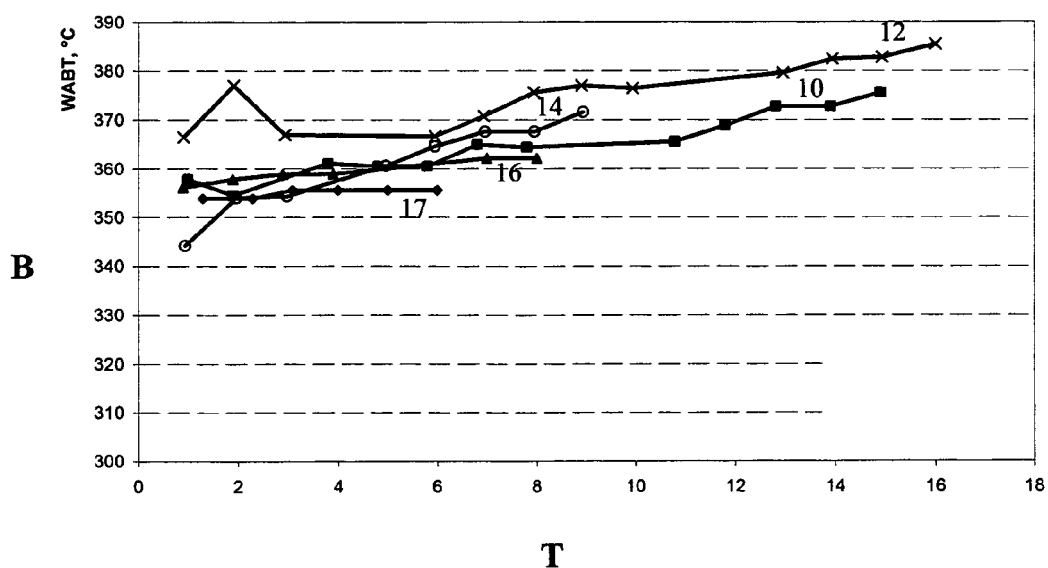
FIG. 2 is a graphical presentation showing the average catalyst temperature as a function of time for various amounts of sulfur employed in the sulfur pre-treatment procedure.

The results of experimental work in terms of the weight average bed temperature (WABT) verses time on stream is shown in FIG. 2. In FIG. 2 the WABT B in ° C. is plotted on the ordinate verses the time T in days on the abscissa. In FIG. 2, the bed temperature for the catalyst without pre-sulfiding is shown by curve 10. The bed temperatures after pre-sulfiding with doses of 3 mole % sulfur with $H_2S$, 10 mole % sulfur with DMDS, 25 mole % sulfur with $H_2S$ and 100 mole % sulfur with $H_2S$ are indicated by curves 12, 14, 16 and 17, respectively. Toluene conversion over the life of these runs was maintained constant at 47% toluene conversion. As shown in the experimental work reported in FIG. 2, the average catalyst bed temperature was maintained within a relatively narrow range over the life of the runs.

Further experimental work employing Catalyst B was carried out to demonstrate the impact of pre-sulfiding on non-aromatics production and average bed temperature on the start-up procedures employing a relatively low hydrogen to toluene low ratio followed by a higher hydrogen to toluene mole ratio as may used in normal toluene disproportionation procedures. In this experimental work the hydrogen to toluene mole ratio was maintained at a value of 1:1 during an initial start-up period of about six days followed by an increase of the hydrogen to toluene mole ratio to a value of 3:1 during the remainder of the run.

Figure 3:
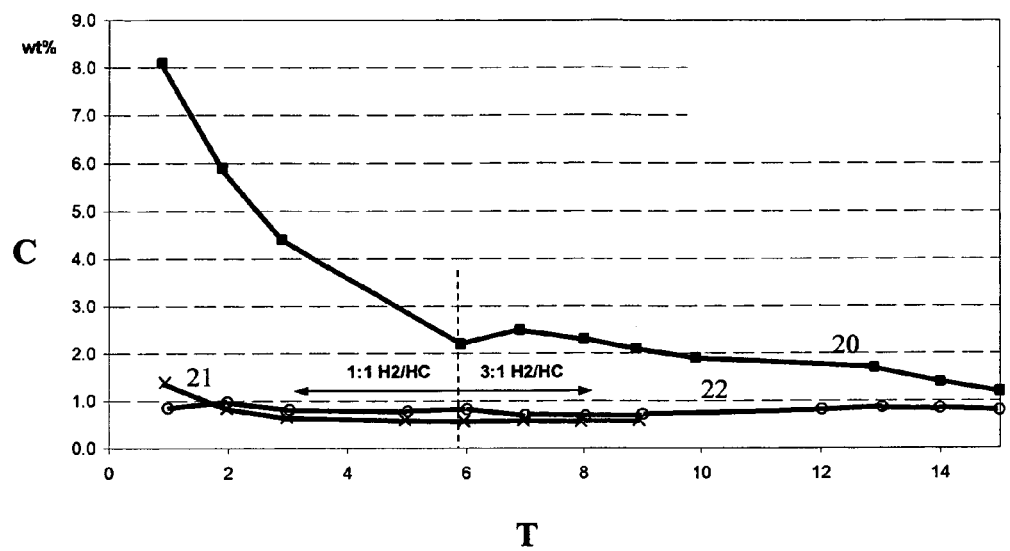
FIG. 3 is a graphical presentation showing the amount of nonaromatics in the liquid toluene disproportionation product for various hydrogen/toluene mole ratios during start-up of the process.
Figure 4:
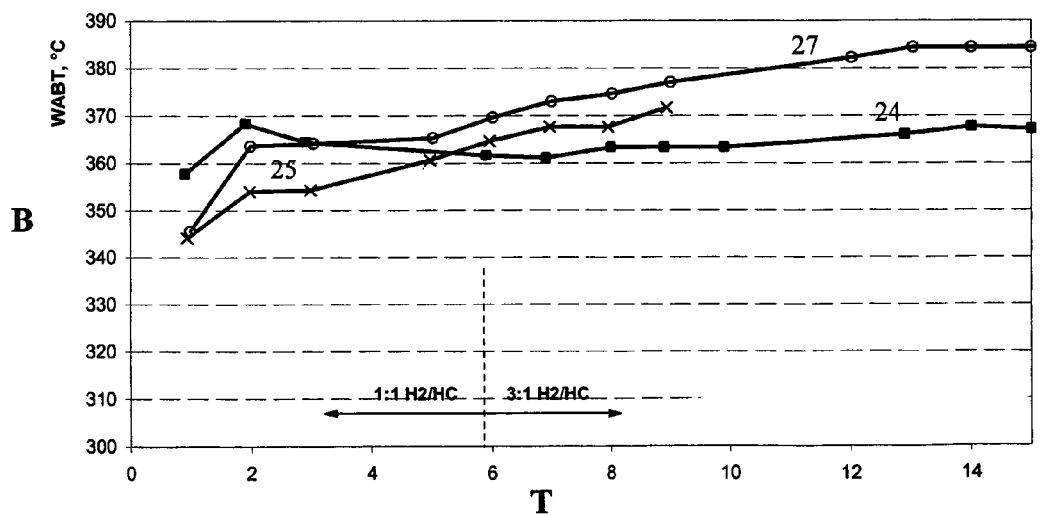
FIG. 4 is a graphical presentation showing the average catalyst bed average temperature as a function of time for different hydrogen/toluene ratios rates during start-up of the toluene disproportionation procedure.

The results of this experimental work are illustrated in FIGS. 3 and 4. In FIG. 3 the wt. % of nonaromatics in the liquid products C is plotted on the ordinate verses the time on stream T in days on the abscissa. In FIG. 3, curve 20 indicates the amount of nonaromatics without pre-sulfiding. Curve 21 indicates the amount of nonaromatics after pre-sulfiding with 50% DMDS mole ratio to nickel with the initial start-up procedure of the hydrogen to hydrocarbon mole ratio of 1:1 followed by an increase in the hydrogen to hydrocarbon mole ratio of 3:1 at day six. Curve 22 shows the corresponding data for pre-sulfiding with 50 mole % sulfur relative to nickel provided by DMDS with the hydrogen to hydrocarbon mole ratio maintained at 3:1 throughout the life of the run. In FIG. 4 the weight average bed temperature B in ° C. is plotted on the ordinate verses time T in days on the abscissa for these same runs, with curve 24 indicating results without pre-sulfiding and curves 25 and 27 showing the results for pre-sulfiding with DMDS at a sulfur dose of 50 mole % sulfur per mole of nickel. Curve 25 corresponds with the results shown in FIG. 3 by curve 21 as achieved by an increase in the hydrogen hydrocarbon mole ratio from 1:1 to 3:1 at about day six. Curve 27 shows the results employing the DMDS at a 50 mole % sulfur dose with the hydrogen/hydrocarbon mole ratio maintained constant at 3:1 over the life of the run.

As illustrated in FIG. 3 the absence of pre-sulfiding resulted in substantially higher nonaromatics content as indicated by curve 20 than for the pre-sulfiding runs depicted by curves 21 and 22. FIG. 4 shows the average bed temperature was maintained at a relatively narrow range with and without pre-sulfiding at a constant toluene conversion of 47%. The data in FIG. 4, like the data in FIG. 2 demonstrates that the pre-sulfiding did not result in a significant loss in catalyst activity.

Having described specific embodiments of the present invention, it will be understood that modifications thereof may be suggested to those skilled in the art, and it is intended to cover all such modifications as fall within the scope of the appended claims.

We claim:

1. A method for the disproportionation of a feedstock containing at least one alkylaromatic compound to produce a transalkylated product comprising:
   (a) providing a mordenite disproportionation catalyst which has been modified by the inclusion of nickel into said catalyst, wherein the catalyst exhibits a silica to alumina molar ratio of less than 9:1;
   (b) pretreating said catalyst by contacting said catalyst under pretreatment conditions at a temperature of at least 100° C. with hydrogen sulfide in an amount effective to passivate a minor amount of active sites provided by nickel in said catalyst and to provide a total sulfur to nickel mole ratio of from 1:1 to 1:10;
   (c) supplying a feedstock containing at least one alkylaromatic compound into contact with said pretreated catalyst under conditions effective for the disproportionation of said alkyl aromatic compound in the presence of hydrogen at a mole ratio of hydrogen and hydrocarbon of about 3:1 to produce a transalkylated product of said alkyl aromatic compound; and
   (d) removing said transalkylation product from contact with said nickel-modified mordenite disproportionation catalyst.

2. The method of claim 1 wherein said mordenite disproportionation catalyst contains nickel in an amount within a range of 0.1-2 wt. %.

3. The method of claim 2 wherein said mordenite disproportionation catalyst contains a second metal selected from the group consisting of a Group 10 metal other than nickel and at least one lanthanide series metal.

4. The method of claim 1 wherein said catalyst is pretreated by flowing a fluid pretreatment stream into contact with said catalyst, said pretreatment stream comprising a minor amount of hydrogen sulfide or a thio compound which is converted to hydrogen sulfide under the pretreatment conditions.

5. The method of claim 4 wherein said pretreatment stream has a sulfur content providing an equivalent hydrogen sulfide concentration within a range of 0.01-20 vol. %.

6. The method of claim 5 wherein said pretreatment stream comprises hydrogen having a hydrogen sulfide content of at least 100 ppm or a thio compound providing an equivalent hydrogen sulfide content of at least 100 ppm.

7. The method of claim 5 wherein said pretreatment stream comprises hydrogen and wherein the hydrogen sulfide or thio compound are selected from the group consisting of hydrogen sulfide, carbon disulfide, a mercaptan, dimethyl sulfide, dimethyldisulfide, and mixtures thereof.

8. The method of claim 1 wherein said feedstock contains toluene and said transalkylated product contains benzene and xylene.

9. The method of claim 1 wherein said feedstock comprises a mixture of trimethylbenzene and toluene and said transalkylated product comprises xylene.

* * * * *